United States Patent [19]

Bessling et al.

[11] Patent Number: 4,732,326

[45] Date of Patent: Mar. 22, 1988

[54] APPARATUS FOR PRODUCING AEROSOLS FROM LIQUIDS

[75] Inventors: Harro A. W. Bessling; Horst E. R. Wandert, both of Brunswick, Fed. Raumfahrt e.V., Fed. Rep. of Germany

[73] Assignee: Deutsche Forschungs- und Versuchsanstalt fur Luft- und Raumfahrt e.V., Del.X

[21] Appl. No.: 877,843

[22] Filed: Jun. 24, 1986

[30] Foreign Application Priority Data

Jun. 28, 1985 [DE] Fed. Rep. of Germany ....... 3523157

[51] Int. Cl.⁴ .............................................. A61M 11/02

[52] U.S. Cl. .................................... 239/338; 239/370; 239/434; 239/555; 261/118; 60/137; 128/200.4

[58] Field of Search ............... 239/338, 366, 370, 423, 239/318, 310, 426, 434, 543, 549, 340, 554, 555, DIG. 7, 369, 371, 337, 346, 413; 431/354; 261/118; 60/726–728; 128/200.14, 200.21, 200.18

[56] References Cited

U.S. PATENT DOCUMENTS

| | | | |
|---|---|---|---|
| 1,478,721 | 12/1923 | Whatley | 239/428 X |
| 2,575,824 | 11/1951 | Maynor | 239/549 X |
| 2,889,998 | 9/1955 | Gallo | 239/549 X |
| 3,077,307 | 2/1963 | Moore et al. | 239/338 |
| 3,914,348 | 10/1975 | Kors et al. | 239/555 X |
| 4,231,973 | 11/1980 | Young et al. | 239/370 X |

FOREIGN PATENT DOCUMENTS

| | | | |
|---|---|---|---|
| 418299 | 10/1934 | United Kingdom | 239/126 |
| 536833 | 5/1941 | United Kingdom . | |

*Primary Examiner*—Andres Kashnikow
*Assistant Examiner*—Kevin Patrick Weldon
*Attorney, Agent, or Firm*—Salter & Michaelson

[57] ABSTRACT

Generator for producing aerosols from liquids including an atomizer mounted in a vessel which is provided with an aerosol outlet. The outlet of the vessel is connected to an ejector operated by a gaseous driving agent. The atomizer is assembled from a plurality of vertically spaced rings with annular liquid outlets, a supply of compressed gas is discharged across the outlets causing the liquid to be drawn upwardly through the outlets.

3 Claims, 11 Drawing Figures

PRIOR ART

| | | | | | |
|---|---|---|---|---|---|
| $d_{p1}$ μm | 2,0 | 2,0 | 5,0 | 5,0 | 5,0 |
| $d_{p2}$ μm | 2,0 | 0,2 | 0,2 | 0,1 | 0,05 |
| $K_0 \cdot 10^9 cm^3/s$ | 0,3 | 1,2 | 2,8 | 7,2 | 22,0 |

APPARATUS FOR PRODUCING AEROSOLS FROM LIQUIDS

BACKGROUND OF THE INVENTION

The invention relates to an apparatus for producing aerosols from liquids, also known as aerosol or particle generators.

Aerosol or particle generators hereinafter called particle generators are very widely used. Generally such a generator includes an atomiser mounted in a vessel, which is provided with a particle or aerosol outlet.

Aerosol or particle gnerators for example are used in air humidifiers, powder production, vacuum drying and inhalation therapy, furthermore in experimental aerodynamics if tracer or light scattering particles are to be fed into a wind tunnel for laser anemometry.

The generation principle used for liquid particles can be ultrasonic, the condensation method or pneumatic atomising. The main operating parameters of a particle generator are the generation rates and the spectrum of particle size with the average diameter.

The use of a generation principle for one of the above depends upon the required particle size and the infeed rate. For inhalation therapy for example droplets of approx. 2 μm diameter are required at an infeed rate of approx. $10^6 s^{-1}$, two of the conditions fulfilled well by ultrasonic atomisation. In laser anemometry the necessary particle diameter depends upon the slip of the particles in the flow. With very large flow vector gradients, as for example in compression shocks, a diameter down to approx. 0.2 μm is required. In a relatively regular flow the particle diameter may reach approx. 2 μm. At higher flow velocities larger particles are required due to the shorter duration of the particles in the laser beam for producing the scattering light photon index. If the particle size cannot be further increased due to the decreasing of slip in the flow then the laser beam power must be increased. The particle size affects the mechanisms in the particle generator due to the coagulation effect.

In smaller wind tunnel systems the particle infeed rate produces no problems but can do in larger plants. Existing generators cannot achieve very high generation rates with very small particle sizes of around 1 μm and less, as are for example desirable for fuel preparation by spraying.

SUMMARY OF THE INVENTION

The invention relates to a generator of aerosol or particles from liquid substances which allows very high infeed rates whilst reducing the coagulation effect and the losses.

Accordingly, it is an object of the present invention to provide a generator for producing aerosols from liquids, including an atomiser mounted in a vessel which is provided with an aerosol outlet, wherein the outlet of the vessel is provided with an ejector operated by a gaseous driving agent.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE PREFERRED EMBODIMENTS

Figure 1:
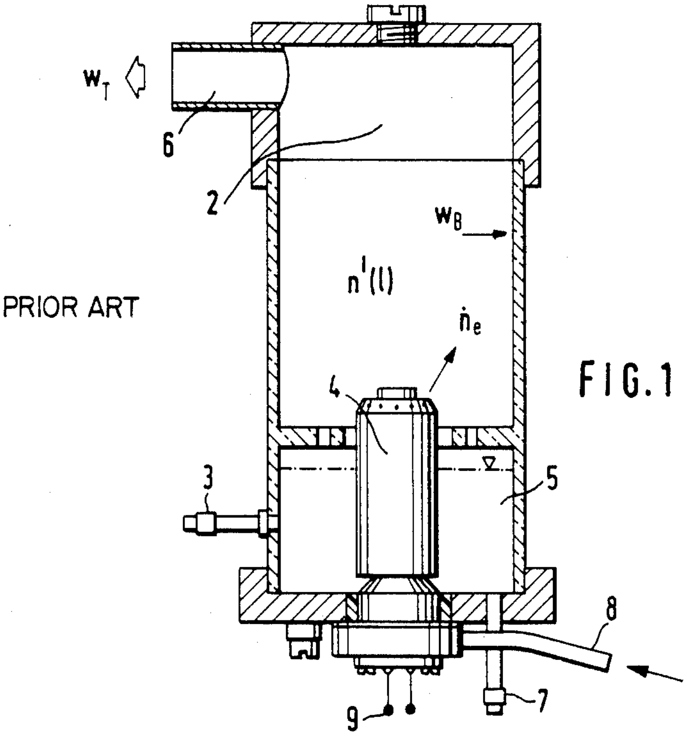
FIG. 1 is a schematic longitudinal section of a prior art particle generator.

This article initially examines the mechanism of losses in a model of an existing particle generator as shown in FIG. 1. This generator to produce particles or aerosols of liquids includes a cylindrical vessel or container 2 and a centrally fitted primary particle emitter or atomiser 4 which includes a number of pneumatic atomiser jets. The aerosol with the particles produced by the atomiser 4 is fed through an outlet tube 6 with a cross-section area F near the top of the container. The liquid to be atomised in the generator is fed through a tube 3 into a liquid storage space 5 up to the level shown by a broken line. The space 5 is provided with a drain connection 7. Compressed air is fed into the atomiser through a tube 8. The atomiser can be provided with an electric heater 9.

When determining the generation rate of a particle generator the adhesion of a part of the particles to the inside wall of the container and the coagulation of particles are considered as losses.

1. Determining the generation rate 1.1 Analysis

For quantitative detection of the generation mechanism initially the particles generated by the atomiser are compared to those particles lost. The total number $n_G(t)$ of the particles in the container at the time t with an outflow rate of $\dot{n}_W$, a loss $\dot{n}_B$, the coagulation $\dot{n}_A$ and the primary generation rate $\dot{n}_e$ is:

$$n_G=\dot{n}_e t-\int \dot{n}_W(t)dt-\int \dot{n}_A(t)dt-\int \dot{n}_B(t)dt. \quad (1)$$

The outflow rate through the tube cross-section F at the velocity $w_T$ and the particle density n' in the generator is:

$$\dot{n}_W=w_T F n'(t). \quad (2)$$

The wall losses $n_B$ result from the size of the particle contact surface $F_B$ in the aerosol container, the velocity $w_B$ of the particles towards the wall and the adhesion factor $\gamma$:

$$\dot{n}_B = w_B F_B \gamma n'(t). \tag{2a}$$

The loss rate $\dot{n}_A$ due to coagulation can be calculated by differentiation of the coagulation formula (3) with the coagulation constant K and the particle density $n'_o$ in the generator at the time $t=0$ as:

$$n' = \frac{n'_o}{1 + n'_o \frac{K}{2} t} \tag{3}$$

and taking the particle numerical density n' into consideration is:

$$n' = n/V_K$$

in the volume $V_K$:

$$\dot{n}_A = \frac{dn_A(t)}{dt} = V_K \frac{dn'}{dt} = -\frac{V_K K}{2} n'(t)^2. \tag{5}$$

By combining the formulae (1) to (5) and multiplication with the factor $1/V_K$ one obtains the particle numerical density:

$$n' = \frac{n_G}{V_K} = \frac{\dot{n}_e}{V_K} t - \frac{w_T F}{V_K} \int n'(t)dt - \frac{K}{2} \int n'(t)^2 dt - \frac{w_B F_B}{V_K} \int n'(t)dt \tag{6}$$

and by differentiation of formula (6) according to time one obtains the differentiation formula of the particle numerical density:

$$\frac{dn'}{dt} = \frac{\dot{n}_e}{V_K} - \frac{w_T F}{V_K} n'(t) = \frac{K}{2} n'(t)^2 - \frac{w_B F_B \gamma}{V_K} n'(t) \tag{7}$$

or with the abbreviations:

$$\frac{K}{2} = A \tag{8a}$$

$$\frac{w_T F + w_B F_B \gamma}{V_K} = B \tag{8b}$$

$$\frac{\dot{n}_e}{V_K} = E \tag{8c}$$

the differentiation formula in the clearer form:

$$\frac{dn'}{dt} = E - Bn' - An'^2. \tag{9}$$

As the solution of these formulae one finds:

$$\frac{dn'}{An'^2 + Bn' - E} + C_1 = -t \tag{10}$$

-continued $$t = \frac{-1}{2\sqrt{(B/2)^2 + AE}} \ln \frac{An' + B/2 - \sqrt{(B/2)^2 + AE}}{An' + B/2 + \sqrt{(B/2)^2 + AE}} + C_1 \tag{11}$$

and with the abbreviation:

$$w = \sqrt{(B/2)^2 + AE} \tag{12}$$

after resolving formula (11) according to n' the form:

$$n'(t) = \frac{W}{A} \cdot \frac{1 + C_2 e^{-2wt}}{1 - C_2 e^{-2wt}} - \frac{B}{2A} \tag{13}$$

The constant $C_2$ can be determined with the starting condition $t=0$, $n'=n'_o$:

$$C_2 = \frac{An'_o + B/2 - W}{An'_o + B/2 + W}. \tag{14}$$

The formulae (13) and (14) give the time characteristics for balancing the numerical particle density:

$$n'(t) = \text{const} = n'_G.$$

The equilibrium is achieved at $t \rightarrow \infty$:

$$n'_G = \underset{t \rightarrow \infty}{n'(t)} = \frac{W}{A} - \frac{B}{2A}. \tag{15}$$

Taking the formulae (8a, 8b, 8c and 12) into consideration the numerical particle density is:

$$n'_G = \frac{w_T F + w_B F_B \gamma}{K V_K} \left( \sqrt{1 + \frac{2 K V_K \dot{n}_e}{(w_T F + w_B F_B \gamma)^2}} - 1 \right) \tag{16}$$

and the generation rate at equilibrium is:

$$\dot{n}_G = n'_o F w_T, \tag{17}$$

$$\dot{n}_G = \frac{F w_T (w_T F + w_B F_B \gamma)}{K V_K} \left( \sqrt{1 + \frac{2 V_K K \dot{n}_e}{(w_T F + w_B F_B \gamma)^2}} - 1 \right) \tag{18}$$

The numerical value of the coagulation constant K included in formula (18) is known if Brownian motion is the surge mechanism. The particle sizes in the generator are distributed over a gauss curve spectrum. A two-particle size classification model is used to simplify calculations. In the aerosol container $V_K$ the turbulence of the flow is considerable and must be taken into account. Practical values are available for the super-imposition of turbulence upon Brownian motion in the flow through smooth tubes. The very complex flow and turbulence conditions in the aerosol vessel $V_K$ can hardly be computed. Estimates of the value of the coagulation constant are then very difficult. However, one can say that an excessive increase in the particle surge index and therefore also coagulation is involved with turbulence. As an initial aid towards analysis of this process the coagulation constant K was multiplied with the factor $S_T$:

$$K = K_o S_T. \qquad (19)$$

With formula (19) and the abbreviations:

$$M = \frac{F_B}{F} w_B \gamma, \qquad (20)$$

$$Z_o = \frac{F^2}{V_K K_o S_T} \qquad (21)$$

$$Z = Z_o (w_T + M)^2 \qquad (22)$$

one obtains the clearer expression:

$$\dot{n}_G = \frac{Z}{1 + M/w_T} \left( \sqrt{1 + \frac{2\dot{n}_e}{Z}} - 1 \right). \qquad (23)$$

Figure 2:
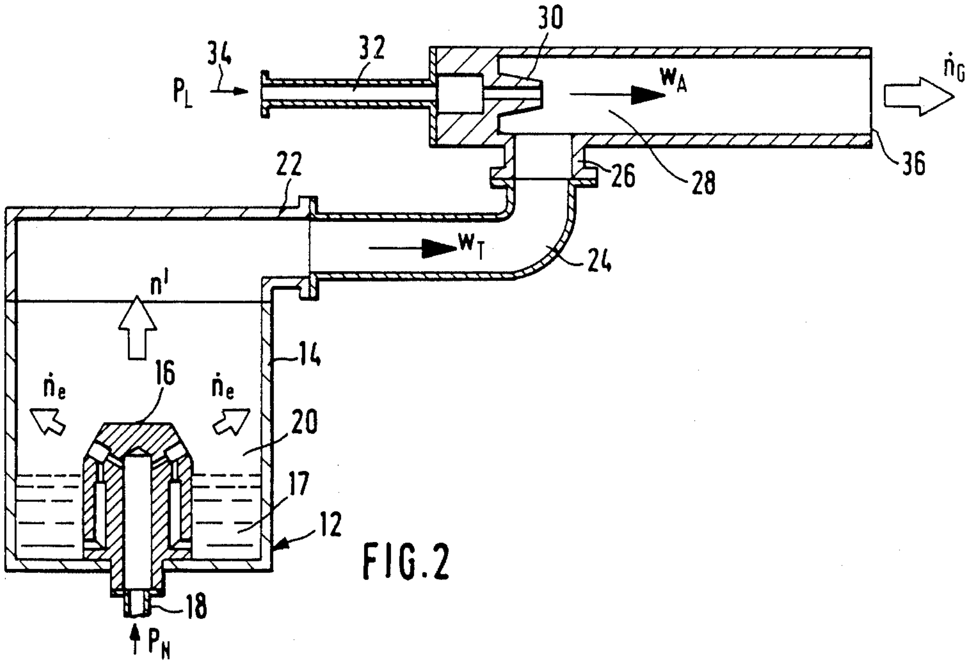
FIG. 2 is a particle generator with an ejector connected to the outlet of the generator.
Figure 3:
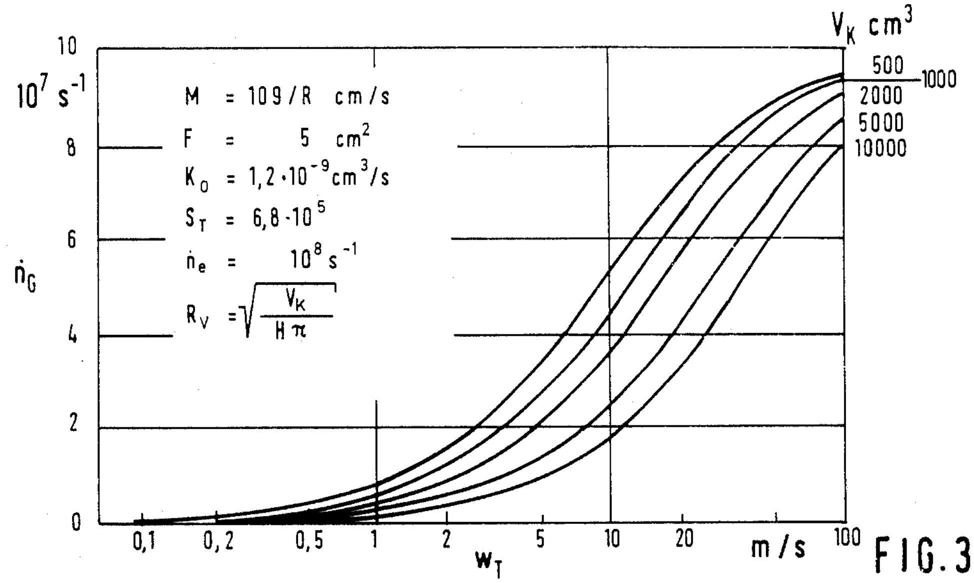
FIG. 3 is a diagram of the relationship between the generation rate $\dot{n}_G$ and the transport velocity $W_T$ with the particle volume $V_K$ as a parameter.
Figure 4:
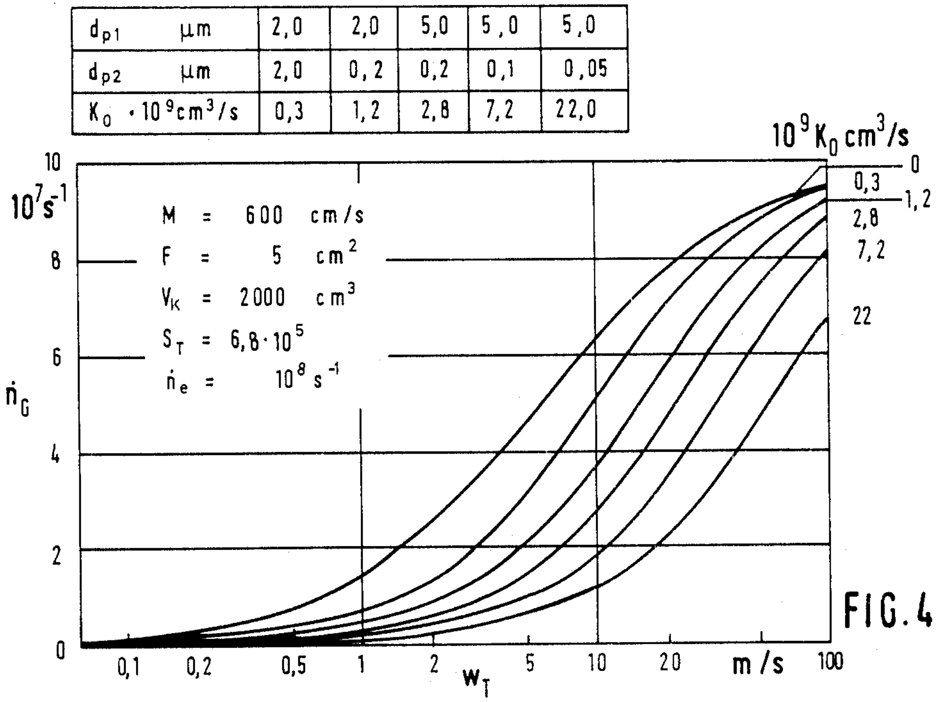
FIG. 4 shows the relationship between the particle generation rate $\dot{n}_G$ and the transport velocity $W_T$ with the coagulation constant $K_o$ as the parameter.
Figure 5:
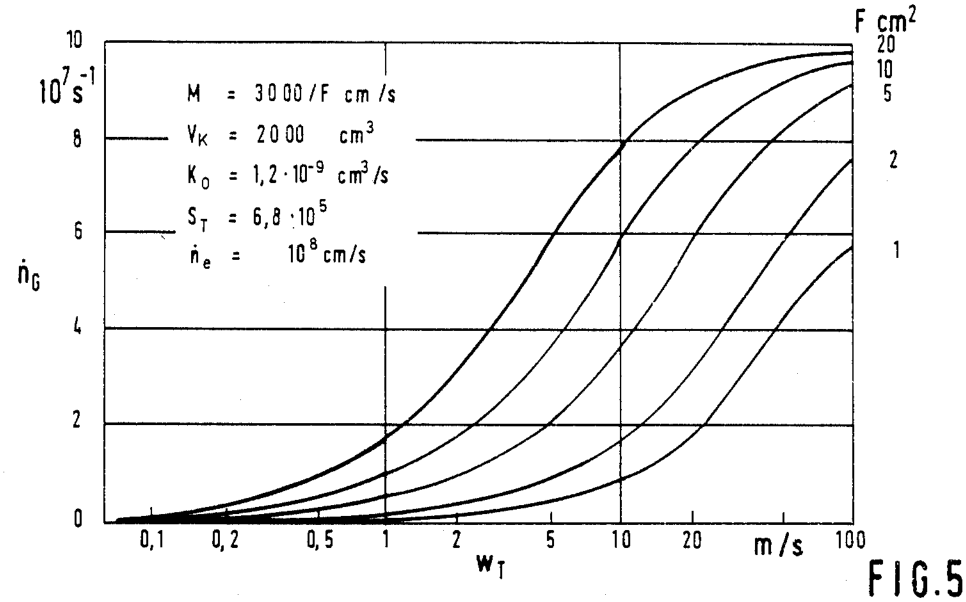
FIG. 5 shows the relationship between the generation rate $\dot{n}_G$ and the transport velocity $W_T$ with the transport cross-section F as the parameter.
Figure 6:
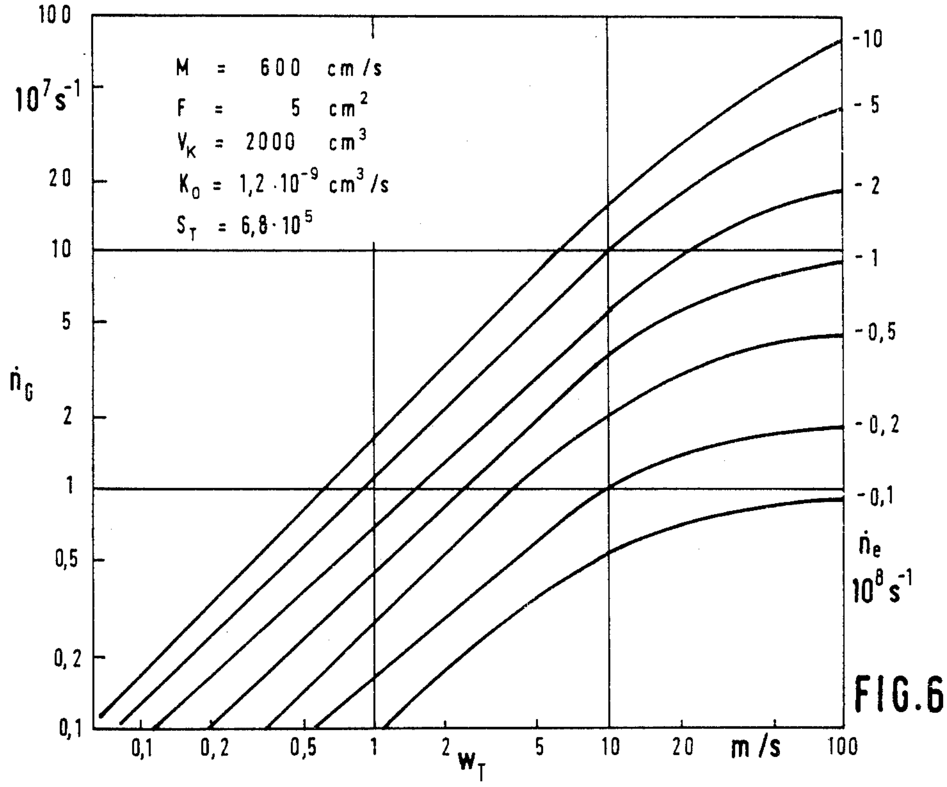
FIG. 6 shows the generation rate $n_G$ as a function of $W_T$ with the parameter $\dot{n}_e$.

The aerosol generator 12 according to the invention is shown in a simplified manner in FIG. 2. The atomiser 16 is fitted on the base of the container 14 and the atomising gas is fed in from below through a tube 18 at a pressure $P_N$. The atomiser 16 is partly submerged in the aerosol liquid 17. In the atomiser area 20 the aerosol particles are present at the primary particle generation rate $\dot{n}_e$ and the numerical particle density n', as indicated by the white arrows.

The outlet 22 of the container 14 is connected to a tube 24 which in turn is connected to the infeed 26 of an ejector apparatus 28. The ejector nozzle 30 connected with a tube 32 feeding a gaseous drive agent with a pressure $P_L$ to the ejector nozzle 30. This produces a generation rate $\dot{n}_G$ with an aerosol transportation velocity $W_T$ and an outlet velocity $W_A$ at the ejector outlet 36. To increase the generation rate the pressure $P_N$ is to be optimized and the pressure $P_L$ is to be increased. By adjusting the pressure $P_L$ the particle outlet velocity from the ejector can be determined. In this way it is possible for example to provide an isokinetic particle infeed into a flowing gaseous medium, thus reducing the slip.

The various operating parameters are shown in FIGS. 3 to 6 described above and therefore require here no further explanation. As indicated, the generation rate can be varied throughout relatively wide ranges.

Devices as shown in FIG. 2 and described above are used to produce very fine aerosols with a high generation rate so that in the wind tunnels stated above the requirements about the aerosol quantity can largely be met. These devices can also be used in medical applications. Devices of this type can further be used for fuel preparation. Such applications are illustrated in FIGS. 7 and 8.

Figure 7:
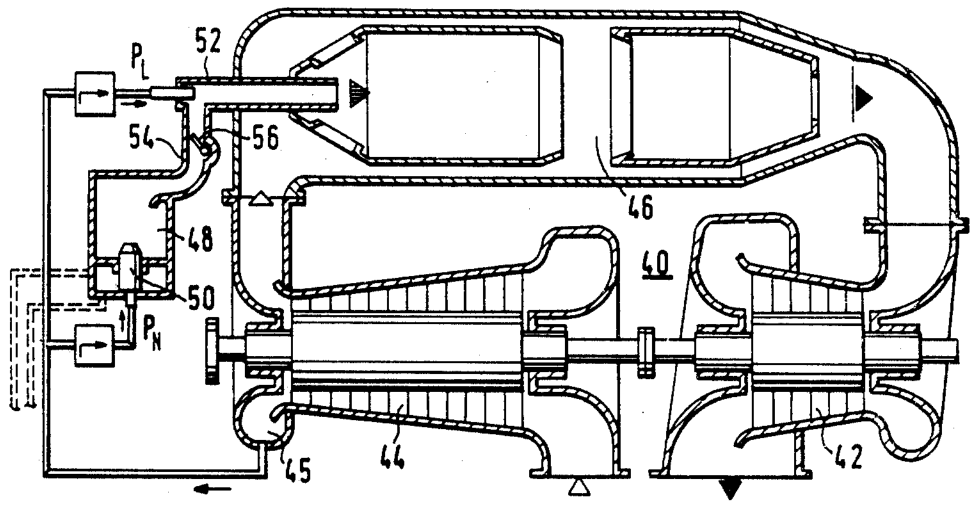
FIG. 7 shows a configuration for fuel preparation for a gas turbine plant.

FIG. 7 shows a schematic of a gas turbine 40 with the turbine 42, the compressor 44 and the combustion chamber 46. The fuel is here prepared by means of an aerosol generator 48 in the principle of a generator as shown in FIG. 2 and described above. The drive agent for the atomiser 50 and the ejector 52 is compressed air taken from the compressor outlet 45 which is fed to the atomiser at the pressure $P_N$ and the ejector 52 at the pressure $P_L$. In addition a throttle 56 is provided in the connection pipe 54.

Figure 8:
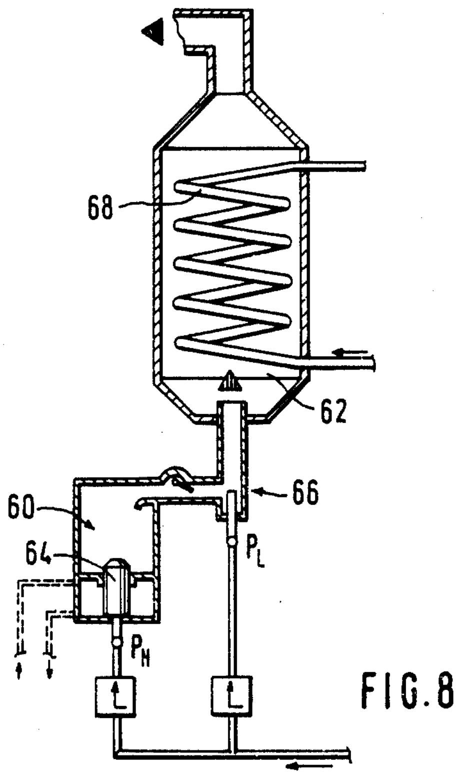
FIG. 8 shows a fuel preparation system for a process heat generator.

In the process heat generator according to FIG. 8 the aerosol generator 60 is designed as per that in FIG. 7. In this embodiment the atomiser 64 and the ejector 66 are pressurized with the same gas, which again is the combustion air as in FIG. 7. In this case the entire additional air is fed to the ejector. If necessary the combustion chamber 62 with the heat exchanger 68 could be provided with an infeed for secondary air in order to ensure full combustion of the fuel.

Figure 9:
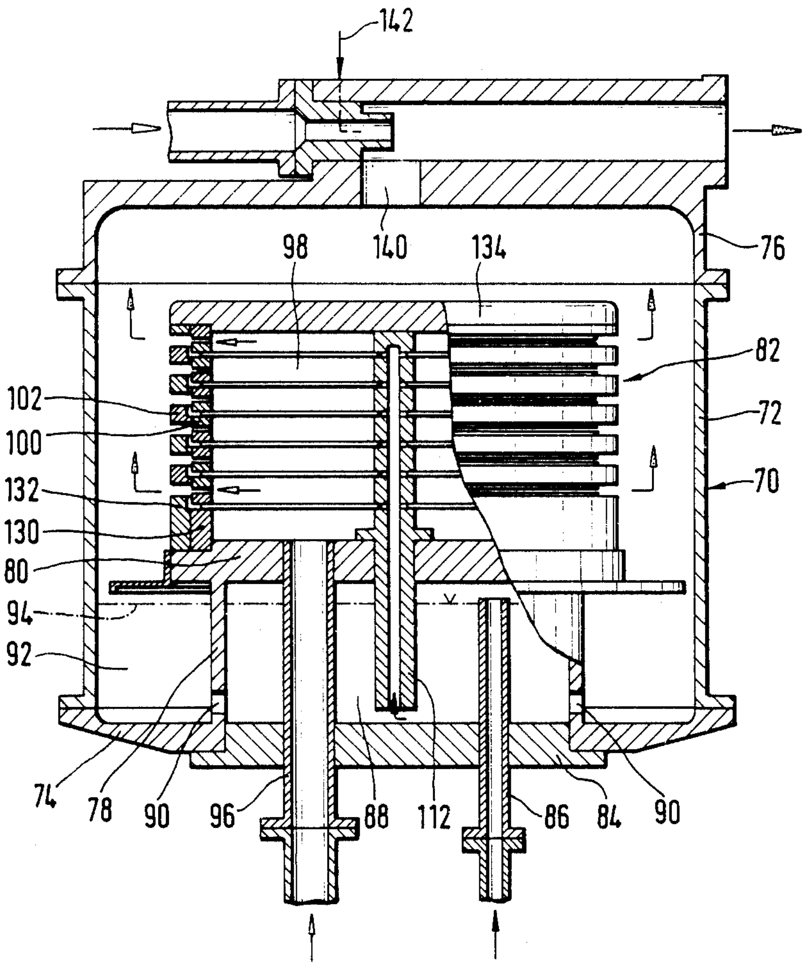
FIG. 9 shows a particle generator provided with a high volume liquid atomiser.
Figure 10:
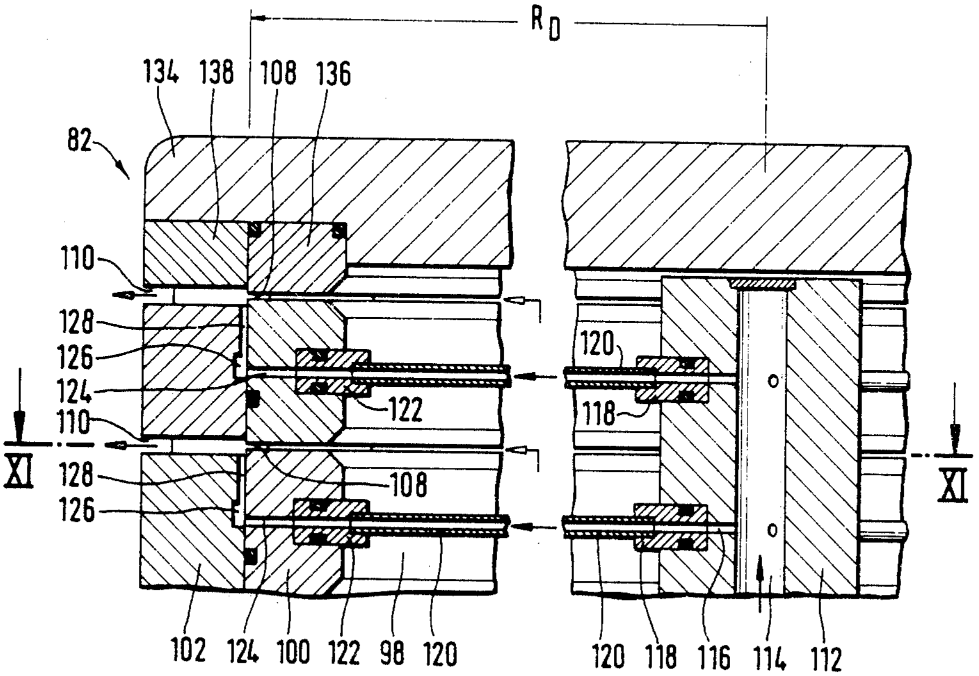
FIG. 10 shows a detail of the atomiser shown in FIG. 9.
Figure 11:
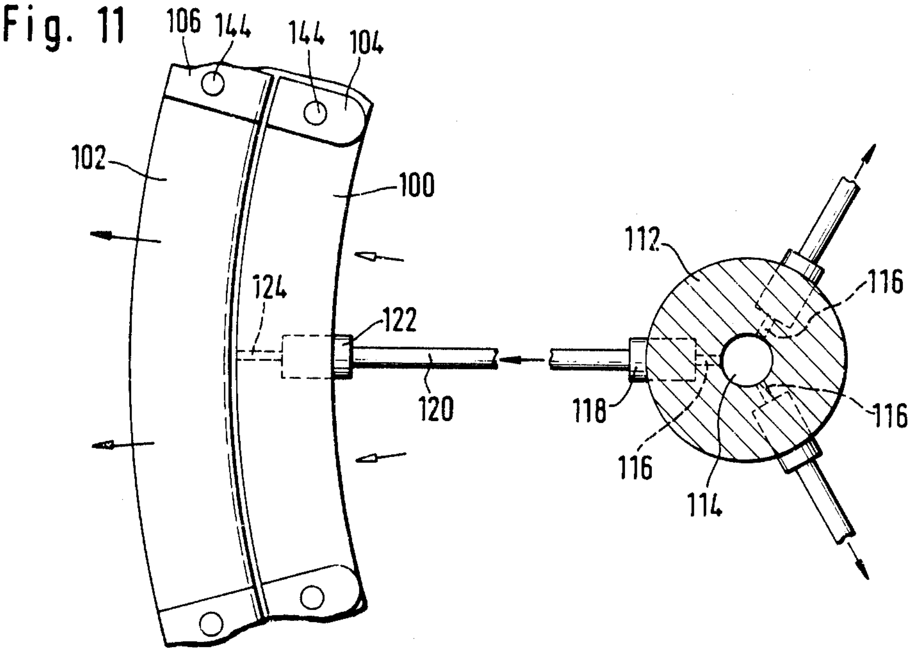
FIG. 11 is a cross-section along line XI—XI in FIG. 10.

For process heat generation or operation of a gas turbine respectively are required high throughput rates for the aerosol generator, i.e. there is necessary a very high particle generation rate. Such a high particle generation rate can be achieved by means of an aerosol generator as shown in FIGS. 9 to 11. The aerosol generator 70 comprises a housing 72 with a base 74 and a cover 76. At a distance above the base 74 a supporting plate 80 for the atomiser 82 is positioned on an annular supporting wall 78. In a detachable central bottom plate 84 is mounted a feed tube 86 for the liquid to be atomised. The liquid flow is shown by an arrow with black arrowhead. The tube 86 leads into the space 88 surrounded by the supporting wall 78. Said space is connected to the outer annular space 92 via connecting openings 90. The spaces 88 and 92 form a storing chamber for the liquid. There is supplied such a quantity of liquid that substantially a liquid level 94 is maintained, which is shown by a dash-dotted line. There may be provided an overflow return connection not shown in the drawing.

There is furthermore provided a pressure gas pipe 96 which is sealed by and lead through the bottom plate 84, the internal liquid chamber 88 and the supporting plate 80 until it reaches the area above the supporting plate 80. Through the pipe 96 pressure gas, preferably compressed air, is fed into the internal chamber 98 of the atomiser. The gas flow is shown by arrows with white arrowheads.

The atomiser 98 has slot-shaped atomiser nozzles. As to be particularly noted from FIGS. 10 and 11, it is constructed by inner rings 100 and outer rings 102, which by spacers 104, 106 are kept at such an axial distance to each other that slot-like discharge openings 108 are formed for the compressed air between the inner rings 100 and slot-like discharge openings 110 for the atomised particles between the outer rings 102, the atomised particles or the aerosol respectively being shown by arrows with arrowheads dotted inside.

In the centre of the supporting plate 80 is provided a feedpipe 112 for the liquid to be atomised. As particularly to be noted from FIGS. 10 and 11, said pipe 112 is provided with an axial bore 114 and with radial bores 116. The radial bores being connected to the bore 114 are arranged at axial distances corresponding to the thickness of the inner rings 100 plus the thickness of the spacers 104. In case of the embodiment are being distributed over the circumference three radial bores each time, as to be noted from FIG. 11. To said radial bores are connected tubes 120 via connecting elements 118 including sealing means, the other end of which is sealingly connected to radial bores 124 in the inner rings 100 via corresponding connecting elements 122. In front of the outlet of said radial bores 124 an annular channel 126 each is provided on the inner circumference of the outer ring 102, which axially is connected to an annular slot 128 ending in front of the air discharge opening 108 formed between the inner rings 100.

The stack of rings 100, 102 is mounted on the supporting plate 80 by means of inner and outer spacing rings 130, 132 while the space 98 surrounded by the rings is closed by a cover 134 on top, which is again resting on the stack of rings with inner and outer spacing rings 136, 138 in between. The ends of the spacing rings 130, 132 and 136, 138 directed towards each other are formed corresponding to the inner and outer rings 100 and 102, so that they form slot-like discharge openings 108 and 110 together with the adjacent rings, the lower outer spacing ring 132 also being provided with the annular channel 126 and the annular slots 128, and the inner spacing ring 130 being provided with openings for the connecting elements for the tubes 120 and the bores 124.

The stack of rings is mounted and compressed by bolts, which may be put through the bores 144 in the spacers 104, 106.

An ejector means is formed by the discharge opening 108 together with the discharge opening 110 and the annular slot 128. By the emerging air beam liquid from the liquid supply with the level 94 is sucked in via the slots 128 and the tubes 120 through the bore 114 and then most finely atomised. The atomisation capacity is determined by the radius $R_D$, on which the liquid is sucked in into the air flow through said ejector means as well as the number of rings placed one above the other. So it is easily possible to determine the desired throughput by increasing the number of rings placed one above the other at a given radius $R_D$.

The very fine particles or the produced aerosol respectively emerging over the circumference of the atomiser 82 are sucked in by means of an ejector 142 from the housing 72 through an opening 140 and supplied to the consumer, in this case the process heat generator or the burners of a gas turbine respectively, as again shown by the arrow with arrowhead dotted inside. The ejector 142 is here moulded to the cover 76.

Just like the ejector according to the embodiment of FIG. 2 the ejector 142 is designed for a capacity corresponding to the generation rate of the atomiser.

What we claim as our invention and desire to secure by Letters Patent of the United States is:

1. A generator for producing an aerosol from a liquid comprising a substantially closed housing having an aerosol outlet, a liquid storage area in said housing for containing a supply of liquid therein, a substantially closed atomizer in said housing above said storage area operative for producing an aerosol from said liquid, and a gas driven ejector operative for withdrawing aerosol from said housing, said atomizer comprising a plurality of pairs of inner and outer rings, said inner and outer rings each having upper and lower surfaces, said pairs of inner and outer rings being placed in closely spaced substantially aligned relation one above another, the inner and outer rings of each pair cooperating to define an annular channel therebetween and an annular slot above the channel thereof, the annular channel of each pair having a substantially closed lower end, the annular slot of each pair communicating with the respective annular channel thereof and having a substantially open upper end which is adjacent the upper surface of the respective outer ring thereof, each of said inner rings having a substantially radially extending bore therein which communicates with the respective channel thereof, the opposed upper and lower surfaces of adjacent inner rings defining slot-like discharge openings therebetween which open outwardly adjacent the upper ends of the respective adjacent annular slots, gas supply means connectable to a supply of pressurized gas for supplying compressed gas to said atomizer so that it passes outwardly through said discharge openings and across the upper ends of said annular slots, and liquid supply means connecting said bores to said liquid storage area so that the passage of gas through said discharge openings and across the upper ends of said annular slots causes said liquid to be drawn upwardly through said liquid supply means into said bores, said annular channels, and said annular slots and to be atomized adjacent the upper ends of said slots.

2. In the generator of claim 1, said liquid supply means comprising a central suction tube communicating with said storage area and extending upwardly therefrom, and a plurality of connecting tubes connecting said suction tube to said radially extending bores in said inner rings for supplying said liquid thereto.

3. The generator of claim 1 further characterized as a generator for preparing fuel for process heat generators or gas turbines.

* * * * *